US007740680B2

(12) United States Patent
Marks

(10) Patent No.: US 7,740,680 B2
(45) Date of Patent: Jun. 22, 2010

(54) AGRICULTURAL COMPOSITION

(75) Inventor: David Marks, Witherslack (GB)

(73) Assignee: Plant Impact PLC (GB)

( * ) Notice: Subject to any disclaimer, the term of this patent is extended or adjusted under 35 U.S.C. 154(b) by 37 days.

(21) Appl. No.: 11/917,268

(22) PCT Filed: Jun. 15, 2006

(86) PCT No.: PCT/GB2006/002185

§ 371 (c)(1),
(2), (4) Date: Jun. 23, 2008

(87) PCT Pub. No.: WO2006/134361

PCT Pub. Date: Dec. 21, 2006

(65) Prior Publication Data

US 2008/0307845 A1     Dec. 18, 2008

(30) Foreign Application Priority Data

Jun. 17, 2005     (GB)     .................. 0512336.9

(51) Int. Cl.
*C05C 9/00*     (2006.01)
*C05C 5/04*     (2006.01)
(52) U.S. Cl. ...................... 71/23; 71/28; 71/30; 71/58; 71/60; 71/63
(58) Field of Classification Search ............... 71/31–63, 71/23, 28, 30
See application file for complete search history.

(56) References Cited

U.S. PATENT DOCUMENTS

| 4,015,970 | A | * | 4/1977 | Hennart | ................... | 71/11 |
| 4,169,717 | A | | 10/1979 | Ashmead | | |
| 4,394,149 | A | * | 7/1983 | Szoka et al. | ................... | 71/28 |
| 4,470,840 | A | | 9/1984 | Welebir | | |
| 4,581,056 | A | | 4/1986 | Nooden et al. | | |
| 4,581,057 | A | * | 4/1986 | Nooden | ................... | 71/28 |
| 4,699,644 | A | | 10/1987 | Brandt et al. | | |
| 6,083,293 | A | | 7/2000 | Bath | | |
| 6,180,569 | B1 | | 1/2001 | Lovatt | | |
| 6,323,394 | B1 | * | 11/2001 | Kumar et al. | ............... | 800/278 |
| 6,358,294 | B1 | * | 3/2002 | Latting | ................... | 71/49 |
| 6,565,860 | B1 | * | 5/2003 | Walker | ................... | 424/400 |
| 6,987,082 | B2 | * | 1/2006 | Tijsma et al. | ............... | 504/101 |
| 7,001,869 | B2 | * | 2/2006 | Johnson | ................... | 504/100 |

2006/0053851 A1 * 3/2006 Johnson ................... 71/23

FOREIGN PATENT DOCUMENTS

| EP | 0114960 A3 | 8/1984 |
| WO | WO 83/02546 A1 | 2/1983 |
| WO | WO 01/22822 A1 | 4/2001 |

OTHER PUBLICATIONS

Database CA [Online], Chemical Abstracts Service, Columbus, OH, US; May 19, 2005. Li, Bin and Jianping Hao, "Study on control release fertilizer with disphenyl urea sulfonic calcium and its effect on growth of *Salvia splendens*." [Abstract] Retrieved from STN accession No. 142:410509. (XP-002400012).
Database WPI Week 199950. Derwent Publications Ltd., London, GB; AN 1999-580998 and CN 1 223 789 A (Univ Shanxi). Jul. 28, 1999. (XP-002400142) Qi, J., et al. [abstract].
Database WPI Week. 200620. Derwent Publications Ltd., London, GB; AN 2006-188086 & JP 2006.055054 A (Taisei Constr CO LTD). Mar. 2, 2006. (XP-002400143) Akiyoshi, M., et al. [abstract].
Yip, Wing-Kin and Shang Fa Yang, "Effect of thidiazuron, a cytokinin-active urea derivative, in cytokinin-dependent ethylene production systems," 1986, *Plant Physiol.*, vol. 80, pp. 515-519.
Mashev, Popov, Nicholov and Vassilev, "Inoculation and Incrustation with Growth Regulators of Seeds To Improve the Free and Symbiotic Nitrogen Fixation," 1987, Proceeding of the IV International Symposium of Plant Growth Regulators. Edited by Lilov, Vassilev, Christov and Andonova, pp. 786-792.
Mashev, Popov, Nicholov and Vassilev, "Treatment of Bean and Non-Bean Plant Seeds with Growth Regulators and Microelements to Improve the Symbiotic and Free Nitrogen Fixation," 1987, Proceeding of the IV International Symposium of Plant Growth Regulators. Edited by Lilov, Vassilev, Christov and Andonova, pp. 777-784.
Andonova and Dencheva, "Influence of Diphenylurea on Mineral Uptake of Maize Following Dryness," 1987, Proceeding of the IV International Symposium of Plant Growth Regulators. Edited by Lilov, Vassilev, Christov and Andonova, pp. 618-622.
El-Keltawi and Croteau, "Salinity Depression of Growth and Essential Oil Formation in Spearmint and Jajoram and Its Reversal of Foliar Applied Cytokinin," 1987, Phytochem., vol. 26, 5, pp. 1333-1334.

* cited by examiner

*Primary Examiner*—Wayne Langel
(74) *Attorney, Agent, or Firm*—Townsend and Townsend and Crew LLP; M. Henry HeinesPla

(57) ABSTRACT

Agricultural compositions which comprises (i) a water-soluble salt of calcium and (ii) an auxin mimic that is an aryl substituted urea, for administering calcium to plants. The compositions particularly include diphenylurea as the auxin mimic. Also formulations containing the compositions and methods of their uses are included.

25 Claims, No Drawings

US 7,740,680 B2

AGRICULTURAL COMPOSITION

CROSS REFERENCE TO RELATED APPLICATIONS

This application is the U.S. National Stage of International Application No. PCT/GB2006/002185, filed Jun. 15, 2006, which claims the benefit of priority of British application number GB 0512336.9, filed Jun. 17, 2005, the disclosures of which are herein incorporated by reference in their entirety for all purposes.

The present invention relates to an agricultural composition, in particular to a fertilizer composition.

Plants need a range of nutrients for healthy growth. These include macronutrients such as nitrogen, phosphorus, potassium, carbon and water, secondary nutrients such as calcium, magnesium, sodium, chloride and sulphur, as well as micronutrients, which include copper, cobalt, iron, manganese, boron, molybdenum, zinc, silicon and nickel.

The introduction of particularly secondary and micronutrients into the plant can be difficult. Even though they may be present in significant quantities in the soil, their availability to the plant may be low.

Calcium is important in maintaining cell wall strength and membrane integrity. Both of these properties are essential in ensuring quality of crops, in particular fruit and vegetables crops, and in providing and maintaining adequate shelf life. Due to a plant's physiology, environment or growing conditions calcium distribution in the plant can be uneven, with areas of localized insufficiency. A plant as a whole may not be calcium deficient, but some part of that plant may be low in calcium causing difficulties to that specific part of the plant. This may occur as calcium uptake and movement within a plant is erratic, with the calcium moving passively through the plant's transpiration stream. This limits the throughput of calcium in areas with low water loss, such as those parts which are shaded or below the ground.

There is, therefore, a need for calcium supplements as a useful tool in improving quality. There are, however, difficulties in getting calcium into plant tissue. Calcium is absorbed into a plant by uptake of water-soluble calcium. Non-water soluble calcium salts, such as calcium carbonate, cannot be absorbed so a calcarious soil environment or the addition of such salts is not of use in overcoming the problem; indeed calcium carbonates can cause root damage.

One of the other factors affecting calcium absorption by and distribution around a plant tissue or organ is the auxin content of that tissue or organ. Auxin is a plant hormone having the chemical name indol-3-acetic acid and is also known as IAA. Areas of the plant that are high in auxin can absorb calcium more readily and act as a sink for calcium in the plant. Some tissues and organs are naturally higher in auxin than others. Seeds, new leaves or shoots, flowers and meristems are all high in auxin and can act as sinks for calcium; whereas mature leaves, roots and stems are all low in auxin content. Dependent on the physiology of the crop, the main sinks for calcium change throughout the season according to the developmental stage of the plant. Crop husbandry can also affect this. By forcing new leaves or flowers, calcium may be taken from other areas of the plant to supply the forced growth leaving those areas low in calcium. Areas of the plant that are low in auxin are often low in calcium, which can lead to a decrease in quality of those areas of the plant. A particular problem occurs where a plant is growing during unusually hot or cold conditions. This is because during high or low temperatures a plant's capacity to produce auxins diminishes, which can reduce calcium transport to meristems and, as calcium is essential to cell division, reduced growth can occur in such conditions.

In the past attempts have been made to overcome low calcium content by supplying auxin exogenously to plant tissue that is low in calcium along with a supply of calcium. Although the plant tissue is able to absorb and hold the calcium supplied in this way, as auxin is a powerful plant hormone this can have deleterious effects on the growth balance of the crop.

There is, therefore, a need of a means of overcoming the problem of supplying calcium to the right part of a plant at the right time.

The applicants have now found an improved manner of administering calcium to plants and, in particular, of supplying calcium to plant tissue low in auxin. They have now found a means of allowing plants to take up and retain calcium in environments or conditions in which they would conventionally not be able to do so.

The present invention provides an agricultural composition comprising: (i) a water-soluble salt of calcium and (ii) an auxin mimic that is an aryl substituted urea.

For use in the present invention suitable water-soluble salts of calcium include nitrates, sulphates and chlorides, with nitrates and chlorides being preferred.

The water-soluble salt of calcium is suitably present in the composition or formulation of the present invention in an amount of up to 15% w/w, preferably from 1 to 15% w/w, more preferably 2 to 15%, e.g. 2 to 10% w/w, and most preferably from 4 to 6% w/w e.g. around 5% w/w.

The water-soluble salt of calcium may be present as a solid powder. It may, for example, be in the form of particles or granules. In this form the water-soluble calcium salt may be coated with the auxin mimic.

The term "auxin mimic" is used herein to mean a compound that is able to produce within a plant one or more of the effects that the plant hormone auxin naturally produces. For the present invention weak auxin mimics are preferred, which are not sufficient to cause an undesirably strong auxin growth response. Particularly preferred are auxin mimics that in addition to their auxin-like properties are also able to produce within a plant one or more of the effects that the plant hormone cytokinin naturally produces. The auxin-like effects of such auxin mimics are counterbalanced by the cytokinin-like properties allowing increased calcium absorption without undesirable growth patterns. The auxin mimic may be a natural or synthetic auxin mimic.

The auxin mimic is an aryl substituted urea.

As used herein, the term "aryl" includes optionally substituted aromatic groups which may be carbocyclic (such as phenyl) or heterocyclic in that they contain, within the ring, one or more heteroatoms such as nitrogen, oxygen or sulphur. An example of a heterocyclic aryl group is pyridyl. Suitable optional substituents for aryl groups include groups such as halo (for example chloro), nitro, hydroxyl (for instance a phenol) and $C_{1-6}$alkyl such as methyl or ethyl. The substituents should be such that the compound retains its property of being an auxin mimic.

Particular examples of aryl groups are optionally substituted phenyl groups.

The aryl substituted urea may be unsymmetrically or preferably symmetrically substituted. Examples include chloropyridyl-phenyl urea (CPPU). The auxin mimic is preferably an unsymmetrically or a symmetrically substituted diphenyl urea (DPU) or a derivative thereof (wherein one or both of the phenyl groups is optionally substituted as described above). Examples include diphenyl urea (DPU), 2-nitro DPU (NDPU), mono- or di-methyl DPU and mono-or di-ethyl DPU. The auxin mimic is most preferably diphenyl urea (DPU), which is also known as carbanilide. DPU is particularly preferred as at low application rates it exhibits cytokinin-like properties, but at higher rates it additionally exhibits auxin-like properties.

A suitable source of the auxin mimic is seaweed extract.

The auxin mimic is suitably present within the composition or formulation of the present invention at a rate of up to 5%, preferably from 0.001 to 5% w/w, and more preferably from 0.005 to 5% w/w, and most preferably from 0.01 to 5% w/w. DPU may be present for example in an applied formulation at a rate of 10 g/L. The auxin mimic may be present in the composition according to the invention at a concentration in the range of 20 to 2000 ppm, and preferably in the range 30 to 300 ppm, most preferably in the range of 20 to 200 pm, e.g. 50 to 100 ppm.

The present invention is advantageous as it leads to increased cellular integrity by preventing areas of local calcium deficiency. Parts of the plant that are low in calcium, particularly those that are to be harvested, can be targeted using the present invention and calcium can be pulled into those parts by increasing calcium uptake by those parts. The present invention allows the plant's calcium sinks to be balanced, allowing the plant to retain applied calcium where it is applied or required. Although conventional calcium fertilisers may be able to increase the calcium content of the whole plant, the present invention allows calcium uptake to be improved in those parts of the plant which are calcium deficient. Resistance to disease such as fungal disease is thereby increased. The present invention is useful in reducing physiological disorders associated with calcium insufficiency including blossom end rot (seen in tomato, pepper, aubergine and cucumber crops), fruit and flower abortion, banana shape, kernel abortion (seen in maize crops) and the disorder hen and chickens (seen in grape crops). It can also lead to improvements in shelf life by enhancing calcium absorption into the harvested parts of a plant. The present invention is also useful in preventing or alleviating disease or infection in plants which occur in areas of local calcium insufficiency, e.g. root diseases, stem rots, pod rots and the like. It can also lead to improvements in calcium related problems in root tubers and stolons of below ground crops. The present invention is particularly advantageous as it allows improved calcium uptake and thereby improved growth habit during unusually hot or cold conditions. It allows plants to absorb calcium in temperatures outside the usual range in which calcium uptake is possible. Conventional calcium fertilisers fail to be taken up in such conditions as the plants auxin production is slowed down or halted. The present invention is particularly advantageous as improvements in calcium uptake can lead to improved food quality.

The compositions of the present invention may also comprise one or more other agriculturally acceptable component. Examples of such components include water, additional nutrient material, weak acids, plant oils, essential oils, metabolic stimulating agents, emulsifiers, thickeners, colouring agents, suspension agents, dispersion agents, carriers or excipients and wetting agents.

Where additional nutrient materials are present they are preferably in the form of a water-soluble salt. Suitably the water-soluble salt of a nutrient mineral is a water-soluble salt of another secondary nutrient, such as magnesium, sodium, chloride and sulphur, or a micronutrient, in particular, copper, cobalt, iron, manganese, boron, molybdenum, zinc, silicon and nickel. The compositions of the present invention are particularly advantageous if they addionally comprise zinc, iron, manganese and/or boron. Particular examples of water-soluble nutrient salts for inclusion in the invention include nitrates, sulphates and chlorides. Specific examples include zinc nitrate, iron sulphate, zinc sulphate, magnesium sulphate, manganese sulphate, iron nitrate or manganese nitrate. The water-soluble nutrient salt, which may be present as a solid powder, is suitably present in the composition in an amount of up to 10% v/v, preferably from 5 to 10% v/v and most preferably from 4 to 6% v/v.

The presence of zinc in the compositions of the present invention is advantageous in cases where the invention is to be used to provide the required calcium supply at low temperatures as zinc can help plants tolerate cool conditions in tender areas of new growth.

In addition, the compositions of the invention may comprise additional nutritional products and/or growth stimulants used in crop nutrition, such as seaweed extract powders, humic and fulvic acid powders and amino acid powders.

Suitable plant oils for inclusion in the compositions of the present invention include canola oil (oilseed rape oil), soybean oil, cottonseed, castor oil, linseed oil and palm oil.

Suitable emulsifiers for use in the compositions of the present invention include any known agriculturally acceptable emulsifier. In particular, the emulsifier may comprise a surfactant such as: typically alkylaryl sulphonates, ethoxylated alcohols, polyalkoxylated butyl ethers, calcium alkyl benzene sulphonates, polyalkylene glycol ethers and butyl polyalkylene oxide block copolymers as are known in the art. Nonyl phenol emulsifiers such as Triton N57™ are particular examples of emulsifiers, which may be used in the compositions of the invention, as are polyoxyethylene sorbitan esters such as polyoxyethylene sorbitan monolaurate (sold by ICI under the trade name "Tween™"). In some instances, natural organic emulsifiers may be preferred, particularly for organic farming applications. Coconut oils such as coconut diethanolamide is an example of such an compound. Palm oil products such as lauryl stearate may also be used.

Examples of thickeners which may be present in the compositions of the present invention comprise gums, for example xanthan gum, or lignosulphonate complexes, as are known in the art. In particular, beet molasses provides a good natural thickener, which also acts as a colourant and a source of plant sugars and hormones. The thickener may be present at a concentration in the range of 0.01 to 1.00% w/w, for example in the range of 0.1 to 0.9% w/w, e.g. around 0.5% w/w.

Suitable suspension agents which may be included in the compositions of the present invention include hydrophilic colloids (such as polysaccharides, polyvinylpyrrolidone or sodium carboxymethylcellulose) and swelling clays (such as bentonite or attapulgite).

Suitable wetting agents for use in the compositions of the present invention include surfactants of the cationic, anionic, amphoteric or non-ionic type, as is known in the art.

Furthermore, the composition suitably comprises a weak acid. As used herein, the expression "weak acid" refers to a weak organic acid such as acetic acid, citric acid, humic acid, fulvic acid or propanoic acid.

The applicants have found that the presence of these acids improve the uptake of nutrients, and particularly nitrogen and secondary or micronutrients, by plants. As a result, the inclusion of these acids brings about beneficial effects. These may include the enhancement of plant growth. More typically, the treatment will improve the quality of plant growth, and specifically the type of growth or growth habit may be enhanced as required. Generally the nutrient content of the plant will be improved as a result of better nutrient uptake and distribution. This is the subject of co-pending British Patent Application No. 0506047.0.

The amount of weak acid, which should be included in the composition is suitably in an amount of from 0.05-3% w/w, for example at about 1% w/w. These relatively small quantities are sufficient to lower the pH of the composition sufficiently to provide for the advantages discussed above.

The compositions of the present invention may further comprise one or more essential oil or active components thereof. The compositions may suitably contain no more than 5% w/w of essential oil, more suitably no more than 3% w/w and preferably no more than 1.5% w/w of essential oil. For instance, the composition may contain no more than 1% w/w essential oil.

As used herein, the expression "essential oil" refers to natural aromatic oils, obtainable from plants. Particular essential oils include tagetes oil, such as the oil obtainable Tagetes erecta and thyme oil, such as the oil obtainable from *Thymus vulgaris*, Wintergreen oil, Rosemary oil, garlic oil, oils from Chenopodium, Erythroxylum, Eugenia, Gaultheria, Myristica, Syzygium, Xanthophyllum, Cinnamonium, Gualtheria, Gossypium and mentha. However, essential oils for inclusion in the compositions of the invention are obtainable from in a wide range of plant families including those families listed in the following Table 1. The Table also includes examples of particular species found within each of these families

TABLE 1

| Family | |
|---|---|
| Acanthaceae | *Adhatoda vasica* (malabar nut) |
| Anacardiaceae | *Anacardum occidentale* (cashew nut) |
| Annonaceae | *Annona reticulata* (bullocks heart) |
| | *Annona squamosa* (custard apple) |
| | *Monodora myristica* (nutmeg) |
| Apiacea (umbelliferae) | *Anethum graveolens* (dill) |
| | *carum carvi* (caraway) |
| | *Carum roxburghianum* (Bishops weed) |
| | *Pimpinella anisum* (aniseed) |
| Apocynaceae | *Nerium oleander* (oleander) |
| Araceae | *Acorus calamus* (flagroot) |
| Asteraceae | *Ageratum conzyaides* (goatweed) |
| | *Artemesia vulgaris* (mugwort) |
| | *Bulmea balsamifera* (camphor) |
| | *Chrysanthemum indicum* (manzanilla) |
| | *Sausurea lappa* |
| | *Hellianthus annus* (sunflower) |
| Brassicaceae | *Raphanus sativus* (radish) |
| Ceasalpinaceae | *Erythrophleum suaveolens* (ordeal tree) |
| Cappardaceae | *Bosica senegalensis* |
| | *Cleome monophylla* |
| Cellastraceae | *Celastrus angulatus* (Chinese bittersweet) |
| Chenopodiacea | *Chenopodium ambrosiodes* (Sweet pigweed) |
| Clusiaceae | *Calophyllum inophyllgum* (luarelwood) |
| Convulvulaceae | *Convulvulus arvensis* (field bindweed) |
| Cucurbitaceae | *Momordica charantia* (Balsam pear) |
| Dipterocarpaceae | *Shorea robusta* (sal tree) |
| Ericaeae | *Gualtheria procumbens* (wintergreen) |
| Euphorbiaceae | *Jatropha curcus* (Physic nut) |
| Fabaceae | *Butea frondosa* (flame of the forest) |
| | *Gliricidia sepium* (Madre de Cacao) |
| | *Psoralea coylifolia* |
| | *Pongamia glabra* (karanja) |
| | *Trigonella foenum* (fenugreek) |
| Graminaceae | *Cymbopgon martini* (gingergrass) |
| | *Oryza sativa* (rice) |
| Laminaeae | *Bystropogon* spp. |
| | *Coleus amboinicus* (oregano) |
| | *Hyptis spicigera* (black sesame) |
| | *Hyptis suaveolens* |
| | *Lavendula angustifolia* (lavender) |
| | *Mentha arvensis* (cornmint) |

TABLE 1-continued

| Family | |
|---|---|
| | *Mentha longifolia* (Horsemint) |
| | *Mentha piperita* (peppermint) |
| | *Mentha spicata* (spearmint) |
| | *Osimum basilicum* (sweet basil) |
| | *Osimum canum* (American basil) |
| | *Osimum kilimandscharicum* |
| | *Osimum suave* (wild basil) |
| | *Origanum vulgarae* (oregano) |
| | *Pogostemon heyneanus* |
| | *Rosmarianus officianis* (rosemary) |
| | *Salvia officianalis* (sage) |
| | *Thymus vulgaris* (garden thyme) |
| | *Tetradenia riparia* |
| Lauraceae | *Cinnamomum aromaticum* (cassia) |
| | *Luaris nobilis* (sweet bay) |
| Liliaceae | *Allium* |
| | *Allium sativum* (garlic) |
| Meliaceae | *Azadirachta indica* (neem) |
| | *Melia azedarach* (Persian lilac) |
| Menisperaceae | *Cissampelos owariensis* (Pareira brava) |
| Myrsinaceae | *Embelia ribes* |
| Myrtaceae | *Eucalyptus* spp. |
| | *Eucalyptus citriodara* (lemon-scented gum) |
| | *Eucalyptus globus* (Blue gum tree) |
| | *Eucalyptus terreticomis* |
| | *Psidium guajava* (guava) |
| | *Syzygium aromaticum* (clove) |
| Myristicaceae | *Myristica fragrans* (mace) |
| Piperaceae | *Piper cubeda* (java long pepper) |
| | *Piper guineense* (Ashanti pepper) |
| | *Piper nigrum* (black pepper) |
| Ranunculaceae | *Nigella sativa* (black cumin) |
| Rutaceae | *Aegle marmelos* (Bengal quince) |
| | *Citrus aurantifolia* (lime) |
| | *Citrus limon* (lemon) |
| | *Citrus paradisi* (grapefruit) |
| | *Citrus sinensis* (sweet orange) |
| | *Limonia acidissima* (roem) |
| | *Zanthoxylum alatum* (prickly ash) |
| Simarubaceae | *Quassia Africana* |
| Solanaceae | *Capsicum annum* (bell pepper) |
| | *Capsicum frutescens* (Tabasco) |
| | *Lycopersicon esculentum* (tomato) |
| | *Nicotiana tabacum* (tobacco) |
| | *Withania somnifera* (winter cherry) |
| Vebenaceae | *Clerodendron siphonanthus* |
| | *Lanatana camara* (yellow sage) |
| | *Lippia geminata* (wild sage) |
| | *Vitex negundo* (begunnia) |
| Zingiberaceae | *Afromomum melagueta* (grains of pleasure) |
| | *Alpinia galanga* (greater galangal) |
| | *Curcuma longa* (tumeric) |
| | *Zingiber officinale* (ginger) |

The term "active components thereof" refers to the chemicals within the essential oil which give rise to the desired activity in plants. Such activities include metabolic stimulating effects, antimicrobial effects, insect or arachnid killing or repellent effects, antiviral and viral remediation effects. The oils may be present alone or combinations of different oils may be included.

When essential oils are included in the compositions of the present invention they can stimulate the metabolism of the plant to which the composition is applied, thus increasing the uptake and utilization of the calcium either by root uptake or foliar absorption. Preferably the essential oil or active component thereof is selected as being one, which increases plant metabolic activity in a pathway that utilizes calcium. As a result, the plant will absorb more calcium to meet its requirements, and so synergy between the components of the composition can be obtained. For example, wintergreen oil, or similar oils, stimulates the need for calcium and conversely calcium stimulates the need for the compounds present in wintergreen oil. The inclusion of wintergreen oil or a similar oil, or an active component thereof, within the composition of the present invention is, therefore, advantageous.

The main component of wintergreen oil is methyl salicylate, and so this may be used instead of wintergreen oil itself, but other salicylate compounds such as salicyclic acid or esters thereof, in particular alkyl esters such as $C_{1-10}$alkyl esters may be used. Preferably, the salicylate compound used in the composition is in the form of an essential oil as these form a readily useable source of active ingredient, which is miscible with the composition. Examples of essential oils which include salicylic acid or salicylates include wintergreen oil as explained above but also oils from Chenopodium, Erythroxylum, Eugenia, Gaultheria, Myristica, Syzygium, Xanthophyllum, Cinnamonium, Gualtheria, Gossypium and mentha.

A further example would be to incorporate into a composition of the present invention an essential oil which stimulates pathways related to auxin production. Such essential oils could work synergistically to enhance uptake of the calcium.

Apart from essential oils and their active components there exist other agents that may be used in the compositions of the present invention to produce advantageous metabolic stimulating effects. For example, the inclusion of cytokinin in the compositions of the invention may be used to increase the requirement for the calcium.

Essential oils supplied with the calcium can also direct the flow of the calcium supplied, by stimulating local need through upregulation of activity requiring calcium in specific tissues. As an example, cell division increases flow of calcium to meristems, therefore, administration of a composition according to the present invention which includes an essential oil which stimulates cell division to, for example, the leaves of plants will have the effect of increasing the calcium content in the meristems.

In addition, many essential oils have anti microbial or insect or arthropod and nematode repellant or killing activity, and these may be included in the compositions of the present invention.

The agricultural compositions of the present invention may be applied to plants, in particular crop plants, in any conventional manner, e.g. by soil or foliar application. They may be applied to root systems, stems, seeds, grains, tubers, flowers, fruit, etc. as required. Examples of means of application include spraying, e.g. by means of an electrostatic or other conventional sprayer, or drip irrigation methods or fertigation systems, which involve application directly to the soil, so as to allow calcium uptake through the roots.

The compositions of the present invention may be adapted for the means of application, e.g. prepared in a form suited to the required means of application. The compositions of the present invention may take the form of liquid or solid concentrates, which require dilution before application. The compositions may be formed into, for example, water dispersible granules, slow or fast release granules, soluble concentrates, oil miscible liquids, ultra low volume liquids, emulsifiable concentrates, dispersible concentrates, oil in water, and water in oil emulsions, micro-emulsions, suspension concentrates, aerosols, capsule suspensions and seed treatment formulations. Aerosol versions of the compositions may be prepared using a suitable propellant, for example n-butane. The form type chosen in any instance will depend upon the particular purpose envisaged and the physical, chemical and biological properties of the composition.

The compositions of the present invention may be prepared using any conventional techniques and methods. Granules may be, for example, formed either by granulating a composition of the present invention alone or with one or more powdered solid diluents or carriers. Granules of the water-soluble calcium salt may be prepared onto which the auxin mimic, e.g. DPU, may be coated by any suitable conventional means. Dispersible concentrates may be prepared by mixing a composition of the present invention in water or an organic solvent, such as a ketone, alcohol or glycol ether. Suspension concentrates may be prepared by combining the compositions of the present invention in a suitable medium, optionally with one or more dispersing agents, to produce a suspension. One or more wetting agents may be included in the suspension and a suspending agent may be included to reduce the rate of settling.

In a further aspect the present invention provides a formulation for administration to plants or to the environment of plants, the formulation comprising a composition according to the present invention and a medium in which the composition may be dispersed or dissolved.

Suitable mediums include any known dispersants or solvents for the composition, for example water or a water miscible liquid, such as n-propanol. The medium is preferably such as to provide formulations that may be used in non-pressurised, hand-actuated spray pumps. The medium is preferably a solvent and most preferably water.

The amount of dispersant or solvent, e.g. water, used will depend upon the particular mode of administration of the formulation and to where it is being applied. In general, a formulation according to the present invention may contain from 10-20% v/v of the composition of the present invention with the remainder being dispersant or solvent, e.g. water.

In yet a further aspect the present invention provides a method for supplying calcium to plants, which method comprises applying to plants or to the environment of plants a composition or formulation according to the present invention.

The present invention is suitable for use on most crops, but in particular can be used for the treatment of greenhouse crops, vegetables, and fruit crops.

The present invention has the following specific uses. When applied to tubers, flowers or fruit it can alleviate or prevent blossom end rot and Bitter Pit in apples. When applied to root systems, such as bulb onions it can minimise root disease and reduce root exudates. When applied to stems, in particular Cocoa plant stems, it can minimise Black Pod and Frosty Pod. When applied to basal stem roots, e.g. those of oil palms, it can increase resistance to disease. It is also of use in the cultivation of foliage crops such as tea and of seed or grain crops such as rice, wheat or cereal.

The amount of composition or formulation applied in any particular situation will vary depending upon a number of factors such as the nature of the crop and the level of calcium required. Typically, where the composition or formulation is in the form of a solution the amount of solution applied is sufficient to provide a solution concentration sprayed to run-off-rate of between 2 ml/lt and 20 ml/lt. In a particular embodiment, the invention provides the use of a composition or formulation according to the present invention as a fertilizer, for administration to crops at a rate of from 1 to 30 liters per hectare, and preferably from 1 to 10 liters per hectare.

The compositions and formulations may be used either alone (and in this case, they may be suitable for organic growers) or in conjunction with other agrochemicals such as fungicides, insecticides or acaricides.

According to another aspect of the present invention there is provided a method for enhancing the uptake of calcium by plants, which method comprises applying to the plants or to the environment thereof a composition which comprises: (i) a water-soluble salt of calcium and (ii) an auxin mimic that is an aryl substituted urea.

According to another aspect of the present invention there is provided a method for increasing cellular integrity by preventing areas of local calcium deficiency which method comprises applying to the plants or to the environment thereof a composition which comprises: (i) a water-soluble salt of calcium and (ii) an auxin mimic that is an aryl substituted urea.

According to another aspect of the present invention there is provided a method for reducing physiological disorders associated with calcium insufficiency which method comprises applying to the plants or to the environment thereof a composition which comprises: (i) a water-soluble salt of calcium and (ii) an auxin mimic that is an aryl substituted urea.

According to another aspect of the present invention there is provided a method for improving shelf life of a harvested crop by enhancing calcium absorption into the harvested parts of a plant, which method comprises applying to the plants or to the environment thereof a composition which comprises: (i) a water-soluble salt of calcium and (ii) an auxin mimic that is anaryl substituted urea.

According to another aspect of the present invention there is provided a method for preventing or alleviating disease or infection in plants which occur in areas of local calcium insufficiency, which method comprises applying to the plants or to the environment thereof a composition which comprises: (i) a water-soluble salt of calcium and (ii) an auxin mimic that is an aryl substituted urea.

According to another aspect of the present invention there is provided a method for improving calcium uptake and/or growth habit during unusually hot or cold conditions, which method comprises applying to the plants or to the environment thereof a composition which comprises: (i) a water-soluble salt of calcium and (ii) an auxin mimic that is an aryl substituted urea.

According to another aspect of the present invention there is provided the use of a composition or a formulation according to the present invention as a fertilizer for administration to crops.

The invention will now be particularly described by way of the following non-limiting examples.

EXAMPLE 1

The following composition was prepared as described:

| Raw Material (Mix Order) | Specification | % w/w formulae |
|---|---|---|
| Analysis: Ca 5% w/w, 50 ppm Diphenylurea | | |
| $H_2O$ | | 56.400 |
| Citric acid | | 00.100 |
| Seaweed extract | | 00.500 |
| 0.2% w/w DPU solution in Ethanol | 0.2% w/w N, N Diphenylurea dissolved in Ethanol equivalent to 50 ppm (0.005% w/w) DPU. | 02.500 |
| Calcium Chloride | 13% Ca | 40.000 |
| Molasses | Beet molasses | 00.500 |

The composition was prepared by adding water to a vessel, ensuring that the temperature of the water is at least 20° C. This was then stirred with a mixer to achieve a reasonable vortex (approx 100-200 rpm), upon which citric acid was added and mixed until dissolved. Thereafter, seaweed extract was added to the vessel, and again, mixing was continued until it had dissolved. Thereafter diphenylurea (DPU) in ethanol solution was added to the vessel and mixed for 10 minutes until dissolved. Next, the calcium chloride liquor was added to the vessel, and mixed until dissolved, and finally the beet molasses was added to the vessel and the solution mixed for 30 minutes before packaging.

EXAMPLE 2

Using a similar procedure to that described in Example 1, the following composition was prepared:

| Raw Material (Mix Order) | Specification | % w/w formulae |
|---|---|---|
| Analysis: Ca 5% w/w, 250 ppm Diphenylurea | | |
| $H_2O$ | | 53.900 |
| Citric acid | | 00.100 |
| Seaweed extract | | 00.500 |
| 0.5% w/w DPU solution in Ethanol | 0.5% w/w N, N Diphenylurea dissolved in Ethanol equivalent to 250 ppm (0.025% w/w) DPU. | 05.000 |
| Calcium Chloride | 13% Ca | 40.000 |
| Molasses | Beet molasses | 00.500 |

EXAMPLE 3

Using a similar procedure to that described in Example 1, the following composition was prepared:

| Raw Material (Mix Order) | Specification | % w/w formulae |
|---|---|---|
| Analysis: Ca 5% w/w, 2000 ppm Diphenylurea | | |
| $H_2O$ | | 18.900 |
| Citric acid | | 00.100 |
| Seaweed extract | | 00.500 |
| 0.5% w/w DPU solution in Ethanol | 0.5% w/w N, N Diphenylurea dissolved in Ethanol equivalent to 2000 ppm (0.2% w/w) DPU. | 40.000 |
| Calcium Chloride | 13% Ca | 40.000 |
| Molasses | Beet molasses | 00.500 |

EXAMPLE 4

Using a similar procedure to that described in Example 1, the following composition was prepared:

| Raw Material (Mix Order) | Specification | % w/w formulae |
|---|---|---|
| Analysis: Ca 9%, 100 ppm Diphenylurea | | |
| $H_2O$ | | 37.400 |
| Citric Acid | | 00.100 |
| Seaweed extract | | 00.500 |
| 0.4% w/w DPU in Isopropyl Alcohol | 0.4% w/w Diphenylurea dissolved in Isopropyl alcohol | 2.500 |

-continued

Analysis: Ca 9%, 100 ppm Diphenylurea

| Raw Material (Mix Order) | Specification | % w/w formulae |
|---|---|---|
| Calcium Nitrate | 15.5% N, 19% Ca Uncoated prills Technical grade | 59.000 |
| Molasses | Beet molasses | 0.500 |

EXAMPLE 5

Using a similar procedure to that described in Example 1, the following composition was prepared:

Analysis: Ca 7%, 100 ppm Diphenylurea

| Raw Material (Mix Order) | Specification | % w/w formulae |
|---|---|---|
| H$_2$O | | 48.400 |
| Citric Acid | | 00.100 |
| Seaweed extract | | 00.500 |
| 0.4% w/w DPU in Isopropyl Alcohol | 0.4% w/w Diphenylurea dissolved in Isopropyl alcohol | 2.500 |
| Calcium Nitrate | 15.5% N, 19% Ca Uncoated prills Technical grade | 37.500 |
| Molasses | Beet molasses | 0.500 |

EXAMPLE 6

Using a similar procedure to that described in Example 1, the following composition was prepared:

Analysis: Ca 5%, Zn 1%, 0.5% Fe 100 ppm Diphenylurea

| Raw Material (Mix Order) | Specification | % w/w formulae |
|---|---|---|
| H$_2$O | | 60.750 |
| Citric Acid | | 00.100 |
| Seaweed extract | | 00.500 |
| 0.4% w/w DPU in Isopropyl Alcohol | 0.4% w/w Diphenylurea dissolved in Isopropyl alcohol | 02.500 |
| Calcium Nitrate | 15.5% N, 19% Ca Uncoated prills Technical grade Ensure CaNO3 is fully dissolved before adding the ZnNO3 | 26.850 |
| Zinc Nitrate | 21.8% Zn Ensure ZnNO3 is fully dissolved before adding the Beet molasses. | 05.000 |
| Iron Nitrate | 13.5% Fe | 03.800 |
| Molasses | Beet molasses | 00.500 |

The following studies have been carried out to determine the effect of the present invention on the growth, health and yield of plants.

Study 1

Low Temperature Study

Method

A trial was set up to evaluate what (if any) difference the application of a formulation based on the present invention made to the growth of crops during low temperatures.

Two formulations were used: Formulation 1 (Inventive), and the same formulation without DPU incorporated (Control). The formulations are shown below:

Formulation 1 (Inventive)

| Material | % w/w |
|---|---|
| Water | 65.05% |
| Citric acid | 00.10% |
| 0.4% DPU in ethanol | 02.50% |
| Calcium nitrate | 26.85% |
| Zinc nitrate hexahydrate | 05.00% |
| Molasses | 00.50% |

Formulation 2 (Control)

| Material | % w/w |
|---|---|
| Water | 67.55% |
| Citric acid | 00.10% |
| Calcium nitrate | 26.85% |
| Zinc nitrate hexahydrate | 05.00% |
| Molasses | 00.50% |

Each formulation was applied to protected strawberry plants grown in a poly-tunnel on a farm in Jordan. Application was as a foliar spray (1 ml/L spray solution, sprayed to run off). The plants were studied during a period of poor weather conditions (abnormally cold), and the plants were evaluated to see what difference (if any) the formulations made to the growth of the plants. Two applications of each formulation were made three weeks apart. The temperature in the day was between 8-12° C. and the temperature at night was between −2-6° C. (for 7 nights the temperature was below zero degrees centigrade).

Results

Measurements were taken a month after the second application of the formulations.

| | Formulation 1: (Inventive) | Formulation 2: Control |
|---|---|---|
| No. of Stems per plant | 24 | 19 |
| Diameter of the crown of the plant | 18 | 12 |
| Colour score* | 4 (mean) | 1 (mean) |
| Leaf size (of | +15% | |

-continued

|  | Formulation 1: (Inventive) | Formulation 2: Control |
|---|---|---|
| Formulation 1 relative to the control) Leaf thickness (of Formulation 1 relative to the control) | +10% | |

*colour score: 0 = 100% green, 5 = 20% green/50% red, 10 = 100% red

Conclusion

The application of a formulation according to the present invention made a clear and obvious difference in the growth of strawberry plants during cold stress. The application of the control formulation did not prevent damage to the strawberry plant caused by cold stress, such as necrosis of leaf margins, abortion of flowers and browning of developing fruit. Colour forms more slowly during cold stress conditions. Relieving cold stress can improve it. The Invention Formulation clearly improved colour formulation.

Study 2

Lettuce Trial

The aim of this trial was to determine the effect of the present invention on plant development in Lettuce (Lactuca sativa sp) using applications at predetermined intervals, and also to evaluate the health of the plants following application and to compare the yield of the treated plot with the control plot.

Method

The trial was carried out in Spain. The area of the plot in which the trial took place is approximately 40,000 m² in the open air. The soil had a free and very loose sandy texture.

The trial plot was divided into 4 sections. Conventional fertilizer and pesticide products were applied to the whole plot as a general treatment. The plot was divided into two subplots of 20,000 m² each, named Plot 1 and Plot 2. Plot 1 comprises: PL 1 (treated with a formulation according to Example 1)-10,000 m and Control 1-10,000 m². Similarly Plot 2 comprises: PL 2 (treated with a formulation according to Example 1))-10,000 m² and Control 2-10,000 m².

The following applications were made:

PL 1: formulation of Example 1 (1 lt/Ha)+General treatments.

Control 1: General treatments.

PL 2: formulation of Example 1 (1 l/Ha)+General treatments.

Control 2: General treatments.

Three foliar applications were made at approximately two weekly intervals with dosage rates of 1 L/Ha.

The general treatments were as follows:

| Phosphoric acid | 1 lt/Ha |
| Potassium nitrate | 1 lt/Ha |
| Nitric acid | 12 lt/Ha |
| Calcium nitrate | 13-14 kg/Ha |
| Potassium in solution | 10 lt/Ha |

-continued

| Fungicides | Standards for Lettuce |
| Insecticides | Standards for Lettuce |

Transplanting of the lettuce plants was carried out in week 40. The variety of lettuce used was Iceberg.

Results

The following results were obtained:

A) Plant Development

Measurements of the diameter of each lettuce were taken. This data gives information on plant development from the transplanting date to the measurement date. After transplanting: Five measurements were taken at approximately 2, 4, 6, and 7 weeks after transplanting and average diameters calculated.

The growth in the PL 1 and PL 2 zones was greater when compared with the measurements from the Control 1 and Control 2 zones.

With respect to the average diameters obtained in Plot 1, there was a difference of 6% in plant development in cm. It was higher in the PL 1 zone, in comparison with the Control 1 zone. With respect to the average diameters obtained in Plot 2, there was a difference of 11% in plant development in cm. It was higher in the PL 2 zone, in comparison with the Control 2 zone.

B) Harvest

Harvesting took place in December. Plot 1 was cut in week 51 and Plot 2 in week 52. The weight of the harvested lettuce plants was measured and average weights calculated.

There was a 10% difference in weight in gr in the average weights obtained in Plot 1. It was higher in the PL 1 zone in comparison with the Control 1 zone.

There was a 5% difference in weight in gr in the average weights obtained in Plot 2. It was higher in the PL 2 zone in comparison with the Control 2 zone.

C) Disease Resistance

There was a small outbreak of tip burn in the trial plot. Tip burn manifests itself as a burn at the tip of the youngest leaves, resulting from poor translocation of calcium to the affected tissues. Environmental factors such as high temperatures and low relative humidity and agricultural factors such as salinity (soil, water, excess nitrogen and potassium deficiency, etc.), calcium-poor soils and water stress, are directly responsible for tip burn. Leaves with tip burn have an unpleasant appearance and the edge of the damaged leaf is weaker and subject to rotting. The salinity of the water in the area in which the trial was held is very high. In Plot 1 ridge soil and plants were swept along as a result of a heavy storm during the trial.

The percentage of lettuce plants affected by tip burn in Plots 1 and 2. were calculated after the first incidence of tip burn was spotted.

Plot 1:

PL1: subplot with 10% tip burn after counting the plants at random.

Control 1: subplot with 15% tip burn after counting the plants at random.

Plot 2:

PL2: subplot with 10% tip burn after counting the plants at random.

Control 2: subplot with 10% tip burn after counting the plants at random.

D) Post-harvest Conservation

An important aspect of cultivation is the length of time the product, here iceberg lettuce, can be kept in transit to the consumer. To assess this, samples were taken at random from the various plots and subplots; these samples were lettuce hearts pre-packed for keeping in cold store prior to sale. The samples were kept in storage at an ambient temperature varying between 5 and 12° C., from the date of cutting to their evaluation in week 8, at which time many of the hearts were unusable due to rotting of the leaves.

The percentages of lettuce hearts in good condition in week 8, from Plots 1 and 2 were determined.

Plot 1: Cutting carried out in week 51, evaluation 9 weeks later.

PL1: subplot with 80% of lettuce hearts in good condition. Of this percentage 40% are fit for consumption, the rest are suffering from rot.

Control 1: subplot with 40% of lettuce hearts in good condition. Some of the remaining percentage were suffering from rot.

Plot 2: Cutting carried out in week 52, evaluation carried out 8 weeks later.

PL2: subplot with 20% of lettuce hearts in good condition. Some of the remaining percentage were suffering from rot.

Control 2: subplot with 0% lettuce hearts in good condition.

Conclusion

A) Plant Development

The increase in plant growth observed in the plants treated according to the present invention is significant. It could allow the cutting date (i.e., harvesting) to be brought forward.

B) Harvest

The increase in yield observed in the plants treated according to the present invention is significant.

C) Disease Resistance

The plants in Plot 1 treated according to the invention had a greater resistance to the disease Tip Burn.

D) Post-harvest Conservation

In plot 1: in PL 1, 40% of lettuce hearts were in good condition, higher than in Control 1, 9 weeks from cutting. In plot 2: in PL 2, 20% of lettuce hearts were in good condition, higher than in Control 2, 8 weeks from cutting. In subplot PL 1, there were 40% more edible lettuce hearts compared with the control subplot. The improvement in 'shelf-life' observed in the plants treated according to the present invention is significant.

Study 3

Bitter Pit Trial on Apples

The aim of this trial was to determine the effect of the present invention on Bitter Pit in apples. Bitter Pit is a disorder found in apples that causes economic loss. Bitter Pit is caused by a deficiency of calcium, and can be reduced by applying calcium fertilisers. However, as the fruit is poor at absorbing calcium it requires multiple applications at high levels to reduce bitter pit.

This trial compares the performance of a formulation according to the present invention at reducing a calcium deficiency (Bitter Pit) to a similar formulation without DPU.

Method

Design: Var Orin 2-3 m 2 trees×3
Sprayed at 14 days after blossom (fruit 3-7 mm)
Spray 600×solution, 3000 L/ha (5 L/ha)

Results

|  | Inventive treatment | | | Control | | |
| --- | --- | --- | --- | --- | --- | --- |
|  | A | B | C | A | B | C |
| Total fruit | 49 | 69 | 60 | 53 | 72 | 63 |
| No bitter Pit (Oct 25) | 1 | 1 | 8 | 0 | 13 | 14 |
| No. bitter pit (Nov 11) | 2 | 2 | 10 | 1 | 17 | 16 |
| average |  | 7.9 |  |  | 17.0 |  |

Inventive treatment is 5% Calcium with DPU (formulation according to Example 1)
Control is 5% Calcium no DPU Conclusion The formulation according to the present invention reduced bitter pit, a disorder caused by calcium deficiency to a greater level than with a similar formula without DPU.

This demonstrates that the present invention improves calcium uptake by the apple plants and can help improve disease resistance.

The formulation according to the invention gave twice the level of reduction of Bitter Pit in apples that is usually seen with other conventional Calcium fertilisers, despite using only one application (standard practice is 20 applications), and having a lower calcium content (most products have>7% Ca).

Study 4

Cucumber Trial

A trial was conducted to determine the effect of applications of the present invention, on the growth and yield of cucumber (*Cucumis sativa*) grown in plastic greenhouses in Andalusia, Spain. The inventive formulation products were added into the drip-irrigation system (a system known as 'fertigation') alongside the reference (control) fertiliser and were applied every seven days at a rate of 5 L formulated product/ha. The reference fertiliser alone and a water-only control were also tested.

Assessments of phytotoxicity and fungal disease were made at the start and the end of harvest and quantitative assessments of yield (number and weight of fruits) were made at each harvest date.

Method

Cucumber plants (*Cucumis sativa*)—variety 'Edona'—were cultivated in a greenhouse according to local agricultural practices. The crop was planted at the test site at an equivalent standard plant density of 25,000 plants per hectare. The Inventive Formulation was made according to Example 1. Three reference fertilisers were used during the season. These were Ammonium nitrate (33% N), Calcium nitrate (15.5% N, 28% Ca) and Potassium nitrate (13% N, 46% K).

The test design was a randomised complete block with 3 replicates for each treatment. Each 4.8 m² plot consisted of two rows, 2.4 m in length and 2.0 m apart. Twelve cucumber plants were planted in each plot. The distance in between the plots and the field edge was at least 3 m.

A reference fertiliser was applied every seven days within the drip irrigation system ('fertigation'). The emitter spacing was 20 cm and the flow rate of each emitter was 1 L per hour. The total amount of nitrogen applied over the growing season within the reference fertiliser programme was 300 kg N/ha. The distribution of nitrogen applied each week (from 2 weeks after planting) in the form of a reference fertiliser is summarised below.

| Week of application | % of Total N | Kg N/ha | Reference fertiliser |
|---|---|---|---|
| 1 | 5 | 15 | Calcium nitrate |
| 2 | 5 | 15 | Calcium nitrate |
| 3 | 10 | 30 | Ammonium nitrate |
| 4 | 10 | 30 | Potassium nitrate |
| 5 | 15 | 45 | Ammonium nitrate |
| 6 | 15 | 45 | Potassium nitrate |
| 7 | 10 | 30 | Calcium nitrate |
| 8 | 10 | 30 | Potassium nitrate |
| 9 | 10 | 30 | Ammonium nitrate |
| 10 | 5 | 15 | Potassium nitrate |
| 11 | 5 | 15 | Potassium nitrate |

The test comprised treatments summarised below.

| Treatment | Treatment Description | Rate Formulated product/ha |
|---|---|---|
| 1 | Inventive Formulation plus reference fertiliser | 5 L/ha |
| 2 | Reference fertiliser | Standard label rate |
| 3 | Untreated - Water only | — |

The test item for treatment 1 was applied alongside the reference fertiliser at each of the 11 application dates. The amount of formulated product for each plot was measured, diluted in 1 L of water and then carefully applied along the irrigation line using the emitter system.

Quantitative assessments of phytotoxicity and fungal disease were made at the start and the end of harvest. Phytotoxicity was rated on vegetables and foliage with a rating scale of 0=no damage to 10=extreme injury (plants dead). Quantitative assessments of total yield (number and weight of fruits) were made at each harvest date. Eleven successive harvests were taken between the seventh and eleventh weeks after planting.

Results

B) Yield

The yield of cucumber fruit in the Inventive Formulation treated plots was consistently higher than those of the water-only treatments, both in terms of number and weight of fruit, at every harvest timing. The total yield obtained is shown below.

| | Treatment | Yield (kg) | Yield (number of fruits) |
|---|---|---|---|
| 1 | Inventive Formulation plus reference fertiliser | 59.96 | 203 |
| 2 | Reference fertiliser | 58.19 | 191 |
| 3 | Untreated - Water only | 45.35 | 151 |

The addition of Inventive Formulation to the standard reference fertiliser programme resulted in an increase in yield compared with that from the reference fertiliser alone. This enhancement, in both the numbers and weight of fruit, was manifest at the earliest and latest harvest timings.

Conclusions

The addition of The Inventive Formulation to the standard reference fertiliser programme resulted in an increase in yield compared with that from the reference fertiliser programme alone. This enhancement, in both the numbers and weight of fruit, was manifest at the earliest and latest harvest timings.

No phytotoxicity or increased susceptibility to fungal disease was observed as a result of treatment with any fertiliser product.

The invention claimed is:

1. An agricultural composition which comprises (i) a water-soluble salt of calcium and (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

2. A composition according to claim 1 wherein the water-soluble salt of calcium is a nitrate, sulphate or chloride.

3. A composition according to claim 1 wherein the water-soluble salt of calcium is present in the composition in an amount from 2 to 15% w/w of the composition.

4. A composition according to claim 3 wherein the water-soluble salt of calcium is present in the composition in an amount from 4 to 6% w/w.

5. A composition according to claim 1 wherein the auxin mimic is a weak auxin mimic that is not able to cause an auxin growth response.

6. A composition according to any one of the preceding claims wherein the auxin mimic is able to produce within a plant one or more of the effects that the plant hormone cytokinin naturally produces.

7. A composition according to claim 1 wherein the auxin mimic is diphenyl urea (DPU), 2-nitro diphenyl urea (NDPU), mono- or di-methyl diphenyl urea or mono- or di-ethyl diphenyl urea.

8. A composition according to claim 1 wherein the auxin mimic is diphenyl urea.

9. A composition according to claim 1 wherein the auxin mimic is present within the composition at a concentration of 20 to 2000 ppm.

10. A composition according to claim 9 wherein the auxin mimic is present at a concentration in the range of 20 to 200 ppm.

11. A composition according to claim 1 which further comprises one or more of the following agriculturally acceptable components: water, additional nutrient material, weak acids, plant oils, essential oils, metabolic stimulating agents, carriers or excipients, emulsifiers, thickeners, suspension agents, dispersion agents or wetting agents.

12. A composition according to claim 11, which comprises a nutrient material, wherein that nutrient material is zinc.

13. A composition according to claim 11, which additionally comprises a weak acid selected from the group consisting of acetic, citric, humic, fulvic and propanoic acid.

14. A composition according to claim 11, which additionally comprises the thickener beet molasses.

15. A formulation for administration to plants or to the environment of plants, comprising a composition according to claim 1 and a medium in which the composition is dispersed or dissolved.

16. A method for supplying calcium to plants, which method comprises applying to the plants or to the environment thereof a composition according to claim 1.

17. A method for fertilizing crops comprising administering to said crop or the soil in which the crop is growing an effective amount of a fertilizer composition according to claim 1.

18. A method for fertilizing crops comprising administering to said crop or the soil in which the crop is growing an effective amount of a fertilizer composition according to claim 15.

19. A method for supplying calcium to plants which method comprises applying to the plants or to the soil in which the plants are growing a formulation according to claim 15.

20. A method for enhancing the uptake of calcium by plants, which method comprises applying to the plants or to the soil in which the plants are growing a composition which comprises:
   (i) a water-soluble salt of calcium and
   (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

21. A method for increasing cellular integrity by preventing areas of local calcium deficiency which method comprises applying to the plants or to the soil in which the plants are growing a composition which comprises:
   (i) a water-soluble salt of calcium and
   (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

22. A method for reducing physiological disorders associated with calcium insufficiency which method comprises applying to the plants or to the soil in which the plants are growing a composition which comprises: (i) a water-soluble salt of calcium and (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

23. A method for improving shelf life of a harvested crop by enhancing calcium absorption into the harvested parts of a plant, which method comprises applying to the plants or to the soil in which the plants are growing a composition which comprises:
   (i) a water-soluble salt of calcium and
   (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

24. A method for preventing or alleviating disease or infection in plants which occur in areas of local calcium insufficiency, which method comprises applying to the plants or to the soil in which the plants are growing a composition which comprises:
   (i) a water-soluble salt of calcium and
   (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

25. A method for improving growth habit during unusually hot or cold conditions, which method comprises applying to the plants or to the soil in which the plants are growing a composition which comprises:
   (i) a water-soluble salt of calcium and
   (ii) an auxin mimic that is an unsymmetrically or a symmetrically substituted diphenyl urea or a derivative thereof wherein one or both phenyl groups are optionally substituted and wherein the auxin mimic is present within the composition at a concentration of 0.001 to 5% w/w.

* * * * *